US012257211B2

(12) United States Patent
Berg et al.

(10) Patent No.: US 12,257,211 B2
(45) Date of Patent: Mar. 25, 2025

(54) MEDICAL FLUID TRANSFER APPARATUS

(71) Applicant: B. Braun Melsungen AG, Melsungen (DE)

(72) Inventors: Karl Martin Berg, Melsungen (DE); Nathanael Fischer, Hauneck (DE); Florin Kopp, Schortens (DE); Konstantin Krug-Sauer, Gudensberg (DE)

(73) Assignee: B. Braun Melsungen AG, Melsungen (DE)

( * ) Notice: Subject to any disclaimer, the term of this patent is extended or adjusted under 35 U.S.C. 154(b) by 585 days.

(21) Appl. No.: 17/606,881

(22) PCT Filed: Apr. 16, 2020

(86) PCT No.: PCT/EP2020/060678
§ 371 (c)(1),
(2) Date: Oct. 27, 2021

(87) PCT Pub. No.: WO2020/221594
PCT Pub. Date: Nov. 5, 2020

(65) Prior Publication Data
US 2022/0211578 A1 Jul. 7, 2022

(30) Foreign Application Priority Data
Apr. 29, 2019 (DE) ............ 10 2019 206 126.5

(51) Int. Cl.
*A61J 1/20* (2006.01)

(52) U.S. Cl.
CPC .......... *A61J 1/2072* (2015.05); *A61J 1/2037* (2015.05); *A61J 1/2048* (2015.05); *A61J 1/2096* (2013.01)

(58) Field of Classification Search
None
See application file for complete search history.

(56) References Cited

U.S. PATENT DOCUMENTS 3,826,261 A * 7/1974 Killinger ............... A61J 1/2096
604/416
3,882,909 A * 5/1975 Ogle ........................ A61J 1/06
141/286

(Continued)

FOREIGN PATENT DOCUMENTS

DE       2652754 A1    5/1978
DE    19507580 A1 *   8/1995 ............... A61J 1/10

(Continued)

OTHER PUBLICATIONS

Search Report received in German Application No. 10 2019 206 126.5 dated Feb. 7, 2020, with translation, 12 pages.

(Continued)

*Primary Examiner* — Susan S Su
*Assistant Examiner* — Katherine-Ph Minh Pham
(74) *Attorney, Agent, or Firm* — Christopher A. Rothe; CM Law (57) ABSTRACT

A medical fluid transfer apparatus for transferring hazardous liquid medication in a fluid-tight manner. The apparatus includes a first connector portion having a first passage for fluid-tight connection to a medical syringe; a second connector portion having a second passage for fluid-tight connection to a medical liquid reservoir; a fluid channel extending between the first passage and the second passage, which permits a fluid-conducting transfer of the medication liquid between the syringe and the liquid reservoir; and an equalization container having an equalization volume, which is connected to the liquid reservoir in a fluid-conducting manner, and which is designed to receive a gas volume displaced during transfer of the medication liquid out of the liquid reservoir. The first passage and the second passage are connected to each other in a fluid-conducting manner via the (Continued)

equalization volume, which forms a fluid channel portion of the fluid channel.

17 Claims, 5 Drawing Sheets

(56) References Cited

U.S. PATENT DOCUMENTS

| | | | |
|---|---|---|---|
| 4,699,615 A | 10/1987 | Fischell et al. | |
| 5,697,919 A * | 12/1997 | Kinoshita | A61M 5/1424 604/185 |
| 6,213,981 B1 * | 4/2001 | Hiejima | A61M 5/1424 604/185 |
| 2013/0228239 A1 * | 9/2013 | Cederschiold | A61J 1/2096 137/497 |
| 2013/0306169 A1 | 11/2013 | Weibel | |
| 2015/0123398 A1 * | 5/2015 | Sanders | F16L 37/0841 285/330 |
| 2017/0333286 A1 | 11/2017 | Phipps | |
| 2020/0238274 A1 | 7/2020 | Breidenbach et al. | |

FOREIGN PATENT DOCUMENTS

| | | | |
|---|---|---|---|
| DE | 19733407 A1 * | 2/1999 | ......... A61M 1/0218 |
| WO | 2012080310 A1 | 6/2012 | |
| WO | 2019072903 A1 | 4/2019 | |

OTHER PUBLICATIONS

Search Report received in International Application No. PCT/EP2020/060678 dated Jun. 2, 2020, with translation, 5 pages.
Written Opinion received in International Application No. PCT/EP2020/060678 dated Jun. 2, 2020, with translation, 16 pages.

* cited by examiner

MEDICAL FLUID TRANSFER APPARATUS

CROSS-REFERENCE TO RELATED APPLICATIONS

This application is the United States national phase entry of International Application No. PCT/EP2020/060678, filed Apr. 16, 2020, and claims the benefit of priority of German Application No. 10 2019 206 126.5, filed Apr. 29, 2019. The contents of International Application No. PCT/EP2020/060678 and German Application No. 10 2019 206 126.5 are incorporated by reference herein in their entireties.

FIELD

The invention relates to a medical fluid transfer apparatus for transferring a health-hazardous liquid medicament in a fluid-tightly sealed manner, having a first connector section, which has a first passage and is provided for fluid-tight connection to a medical syringe, a second connector section, which has a second passage and is provided for fluid-tight connection to a medical liquid container, a fluid channel, which extends between the first passage and the second passage and—in a state of the fluid transfer apparatus in which the latter is connected to the syringe and to the liquid container—allows a fluid-conducting transfer of the liquid medicament between the syringe and the liquid container, and a compensation container with a fluid-tight compensation volume of variable volume, which compensation volume is—in the connected state of the fluid transfer apparatus—connected in a fluid-conducting manner to the liquid container and is configured for receiving a gas volume displaced from the liquid container during the transfer of the liquid medicament.

BACKGROUND

A medical fluid transfer apparatus of said type is generally known in the field of medical technology and may also be referred to as transfer system or closed system transfer device (CSTD). Such fluid transfer apparatuses are intended for use in the preparation of application-ready CMR liquid medicaments, wherein the abbreviation CMR commonly refers to carcinogenic, mutagenic and reprotoxic medicaments.

During the preparation of such a liquid medicament, this is commonly introduced into a medical liquid container, or extracted therefrom, by means of a medical syringe. Here, in order to avoid a health hazard from toxic gases escaping from the liquid container due to being displaced, the known fluid transfer apparatus is intended to allow a fluid-tightly or hermetically sealed transfer of the health-hazardous liquid medicament between the syringe and the liquid container.

For this purpose, the known fluid transfer apparatus has a first connector section with a first passage and has a second connector section with a second passage. The first connector section is provided for fluid-tight connection to the medical syringe. The second connector section is provided for fluid-tight connection to the medical liquid container. The first passage and the second passage are connected to one another in a fluid-conducting manner by means of a fluid channel. Moreover, a compensation container with a fluid-tight compensation volume of variable volume is provided. In a state of the fluid transfer apparatus in which it is connected to the syringe and to the liquid container so as to be operationally ready, the compensation volume is connected in a fluid-conducting manner to the liquid container. The compensation volume serves for receiving a gas volume displaced from the liquid container during the transfer of the liquid medicament from the syringe into the liquid container. In the known fluid transfer apparatus, the compensation container is an elastic bladder which is arranged in a projecting manner in the region of the second connector section, wherein the compensation volume of the bladder is formed away from the fluid channel and separately therefrom.

SUMMARY

It is an object of the invention to provide a medical fluid transfer apparatus of the type mentioned in the introduction that has a simplified construction and at the same time makes possible improved handling.

Said object is achieved in that the first passage and the second passage are connected to one another in a fluid-conducting manner via the compensation volume, wherein the compensation volume forms a fluid channel section of the fluid channel. The solution according to the invention makes it possible in particular to dispense with an arrangement of the compensation volume that is separate from the fluid channel. In this way, a particularly simple construction of the fluid transfer apparatus can be achieved. Since the compensation volume forms a fluid channel section of the fluid channel according to the invention, the compensation volume is accorded a particularly advantageous multiple function. This is so on the one hand because the compensation volume serves for receiving the gas volume displaced from the liquid container. Additionally, the compensation volume acts as a fluid-conducting section of the fluid channel. This multiple function of the compensation volume makes possible in particular the particularly simple construction according to the invention of the fluid transfer apparatus. Moreover, the solution according to the invention makes it possible to avoid in particular an arrangement of the compensation container that projects laterally or in another manner from the remaining sections and/or components of the fluid transfer apparatus. In this way, simplified handling of the fluid transfer apparatus during the preparation of the liquid medicament can be achieved. The first connector section may in particular have a Luer connector, or some other fluid connector, which is configured for fluid-tight connection to a complementary Luer connector, or fluid connector, of the medical syringe. The first passage may extend through the first connector section in particular in the form of a channel or of a lumen. The first passage may act as an inlet or as an outlet of the fluid transfer apparatus according to the flow direction of the liquid medicament during the transfer. The second connector section may in particular have a piercing mandrel which is configured for insertion into a section of the liquid container that is provided for this purpose. Alternatively, the second connector section may have a threaded or plug-in section which is configured for connection to a complementary threaded or plug-in section of the liquid container. The second passage may extend through the second connector section in particular in the form of a channel or of a lumen. The second passage may act as an inlet or as an outlet of the fluid transfer apparatus according to the flow direction of the liquid medicament during the transfer. The fluid channel forms a fluid-conducting connection between the first passage and the second passage. In a state of the fluid transfer apparatus in which it is connected to the syringe and to the liquid container so as to be operationally ready, the liquid medicament can thus, for example, pass via the first passage from the syringe into the fluid channel and, from there, via the second passage into the liquid container, or vice versa. Since the compensation volume forms a fluid channel section of the fluid channel according to the invention, in this case the liquid medicament also flows through the compensation volume.

In one configuration of the invention, the first connector section and the second connector section are arranged on face end regions of the compensation container that are situated opposite one another. In this way, a further simplified construction of the fluid transfer apparatus can be achieved. In this configuration of the invention, the compensation container accordingly also acts as a bearing structure and/or connecting structure, wherein the two connector sections may be fixed indirectly or directly on the compensation container.

In a further configuration of the invention, the compensation container is manufactured from an elastic material and/or has an elastic configuration, whereby, for variation of the volume, the compensation volume can be expanded elastically and/or can be contracted elastically. As an elastic material, an elastomer or some other elastic plastic may in particular be selected. The elastic material preferably has rubber-elastic and/or soft-elastic properties. The alternatively or additionally provided elastic configuration of the compensation container may be achieved in particular by way of a thin-walled design of a container wall. In such a configuration, it is not absolutely necessary for the compensation container to be manufactured from an elastic material. Instead, the compensation container may be manufactured in particular from a dimensionally stable material, for example a dimensionally stable plastic, or from metal. This configuration of the invention makes it possible for the compensation volume of variable volume to be provided with particularly simple structural means.

In a further configuration of the invention, the compensation container is a corrugated bellows. Preferably, the corrugated bellows is manufactured from an elastic material. Alternatively, the corrugated bellows may be manufactured from a thin-walled, dimensionally stable material. For variation of the volume of the compensation volume, the corrugated bellows is, in a basically known manner, axially expandable and/or axially compressible in a concertina-like manner.

In a further configuration of the invention, the compensation container has at least two container parts which are manufactured from a dimensionally stable material and which border the compensation volume and which, for variation of the volume of the compensation volume, are movable relative to one another. The container parts may be manufactured in particular from a dimensionally stable plastic or from metal. Through this configuration of the invention, it is in particular the case that inadvertent damage to the compensation volume and thus health-hazardous contamination of the surroundings with the liquid medicament are counteracted. The at least two container parts may in particular be linearly movable relative to one another. Preferably, the at least two container parts are displaceably fixed on one another. For fluid-tight sealing of the at least two container parts, a separate sealing element may be provided. Alternatively or additionally, the at least two container parts may be fitted together in a fluid-tight manner and so as to be movable relative to one another.

In a further configuration of the invention, for transferring the liquid medicament between the first passage and the second passage, the compensation container can be moved manually by way of pumping. In this configuration of the invention, the compensation container accordingly has a further function. This is because, besides the receiving of the displaced gas volume and the fluid line between the first passage and the second passage, the compensation container additionally serves here for conveyance by way of pumping of the liquid medicament between the first passage and the second passage. For example, the liquid medicament may first be released into the fluid channel via the first passage by means of the syringe. Accordingly, at least a part of the liquid medicament is situated in the fluid channel section formed by the compensation volume. Afterwards, by means of a corresponding manual actuation of the compensation container by way of pumping, the liquid medicament can be conveyed from the compensation volume onward in the direction of the second passage. Here, in order to avoid unwanted flowing of the liquid medicament back in the direction of the first passage, a shut-off or check valve may be arranged in the region of the first passage. This is not absolutely necessary, however. The movability of the compensation container by way of pumping may be achieved in particular by way of an elastic configuration thereof and/or by way of dimensionally stable sections and/or components of the compensation container that are displaceable relative to one another by way of a pumping movement.

In a further configuration of the invention, provision is made of handling surfaces which are connected operatively to the compensation container and which, for the manual pumping movement of the compensation container, are displaceable relative to one another. The handling surfaces may be arranged in particular for radial and/or axial manual action on the compensation container. Preferably, the handling surfaces are arranged on face end regions of the compensation container that are situated opposite one another. The manual pumping movement of the compensation container can preferably be brought about by means of a pressing-together of the handling surfaces between the fingers of one hand. The handling surfaces may be formed directly on the compensation container. Alternatively, the handling surfaces may be formed on sections and/or components that are joined together with the compensation container.

In a further configuration of the invention, provision is made of a spring device which is connected operatively to the compensation container and which imparts a spring force which expands the compensation volume. The spring device serves for simplified movability of the compensation container by way of pumping and has the effect that the compensation volume can, from a manually pressed-together or contracted state, be automatically returned to an expanded state by means of the spring force. The spring device may be formed by way of a corresponding resiliently elastic design of the compensation container and/or by a separate spring element. The spring element is preferably a helical spring.

In a further configuration of the invention, provision is made of a first valve which can be transferred between a blocking position and a throughflow position and by means of which the first passage, in the blocking position, is separated in a fluid-tight manner from the compensation volume and, in the throughflow position, is connected in a fluid-conducting manner to the compensation volume. The first valve may be transferable between the blocking position and the throughflow position by means of manual actuation or automatically. By way of the first valve, it is in particular the case that unwanted flowing of the liquid medicament from the fluid channel or the compensation volume back in the direction of the first passage is counteracted. Moreover, by way of the first valve, a situation in which the liquid medicament undesirably passes through the first passage and into the compensation volume or into the fluid channel can be avoided. In this way, further improved handling can be achieved.

In a further configuration of the invention, the first valve is a shut-off valve configured for manual actuation. Accordingly, the shut-off valve can be transferred manually between the blocking position and the throughflow position.

In a further configuration of the invention, provision is made of a second valve which can be transferred between a blocking position and a throughflow position and by means of which the compensation volume, in the blocking position, is separated in a fluid-tight manner from the second passage and, in the throughflow position, is connected in a fluid-conducting manner to the second passage. The second valve may be transferable between the blocking position and the throughflow position by means of manual actuation or automatically. By way of the second valve, it is in particular the case that a situation in which the liquid medicament can pass from the compensation volume or from the fluid channel section formed by the compensation volume in the direction of the second passage is avoided. Moreover, by way of the second valve, a situation in which the liquid medicament can pass from the liquid container undesirably into the compensation volume or into the fluid channel section is avoided. Through this configuration of the invention, further improved safety in the handling of the fluid transfer apparatus is achieved.

In a further configuration of the invention, the second valve is a pressure valve which, in a manner dependent on a pressure prevailing in the compensation volume, can be transferred automatically between the blocking position and the throughflow position. The pressure prevailing in the compensation volume may be generated in particular by an actuation of the medical syringe. Alternatively or additionally, the pressure may be generated by a manual pumping movement of the compensation container. If the pressure reaches or exceeds a structurally defined limit pressure of the pressure valve, the latter is transferred automatically from the blocking position into the throughflow position. Conversely, upon reaching or dropping below the limit pressure, the pressure valve can be transferred automatically from the throughflow position into the blocking position.

In a further configuration of the invention, in a delivery state of the fluid transfer apparatus, the first valve and the second valve each assume the blocking position, and the compensation volume is filled with a sterile gas. Through this configuration of the invention, it is in particular the case that an unwanted pressing-together or even collapse of the compensation container is counteracted. For this purpose, the compensation volume is filled with the sterile gas and, moreover, is closed off in a fluid-tight manner by means of the first and second valves. In this way, further improved handling can be achieved.

In a further configuration of the invention, provision is made of a latching device which is assigned to the second connector section and which allows a non-detachable latching connection to the medicament container. By means of the latching device, a non-detachable form- and/or force-fitting connection between the fluid transfer apparatus and the medicament container can be achieved. In this way, inadvertent separation during use of the fluid transfer apparatus from the medicament container is avoided. This allows further improved handling of the fluid transfer apparatus with regard to the safety thereof.

BRIEF DESCRIPTION OF THE DRAWING FIGURES

Further advantages and features of the invention emerge from the claims and from the following description of preferred exemplary embodiments of the invention, which are illustrated on the basis of the drawings, in which:

DETAILED DESCRIPTION

As per FIGS. 1-6, a medical fluid transfer apparatus 1 for use in an application-ready preparation of a health-hazardous liquid medicament F (FIG. 3) is provided. The medical fluid transfer apparatus 1 may also be referred to as transfer system or closed system transfer device. The liquid medicament F is a so-called CMR (carcinogenic, mutagenic, reprotoxic) liquid medicament which is intended for use in a cancer therapy. The liquid medicament F can be carcinogenic, mutagenic and/or reprotoxic and consequently has to be classified as hazardous to health.

During the application-ready preparation of the liquid medicament F by medical personnel, the liquid medicament F is fed to a medical liquid container 2, and/or is extracted therefrom, by means of a medical syringe (not illustrated in any more detail in the drawing). Here, in order to avoid a hazard to the health of the medical personnel, contamination of the surroundings with the liquid medicament F must be avoided. The fluid transfer apparatus 1 primarily serves this purpose.

The medical fluid transfer apparatus 1 has a first connector section 3 with a first passage 4 and has a second connector section 5 with a second passage 6.

In the present case, the first connector section is in the form of a Luer lock connection 3, this however not being absolutely necessary. Alternatively, the first connector section 3 may also be in the form of some other fluid coupling that is generally known in the field of medical technology. For fluid-guiding connection to the medical syringe, the Luer lock connection 3 is connected, in a basically known manner, to a complementary Luer lock connection which is arranged on the syringe at the outlet side.

In the present case, the second connector section is in the form of a piercing mandrel 5, which, for fluid-tight connection to the liquid container 2, is inserted through a section of the liquid container 2 that is provided for this purpose and into said liquid container. For this purpose, the liquid container 2 may have for example a pierceable plug, a diaphragm or the like. Such a design is also not absolutely necessary. Instead of the piercing mandrel 5, a screw-type or plug-in connection to the liquid container 2 is in particular also conceivable.

The first passage extends through the first connector section 3 in the form of a lumen 4 extending in an axial direction A. Correspondingly, the second passage extends through the piercing mandrel 5 in the form of a lumen 6 in the axial direction A.

Figure 1:
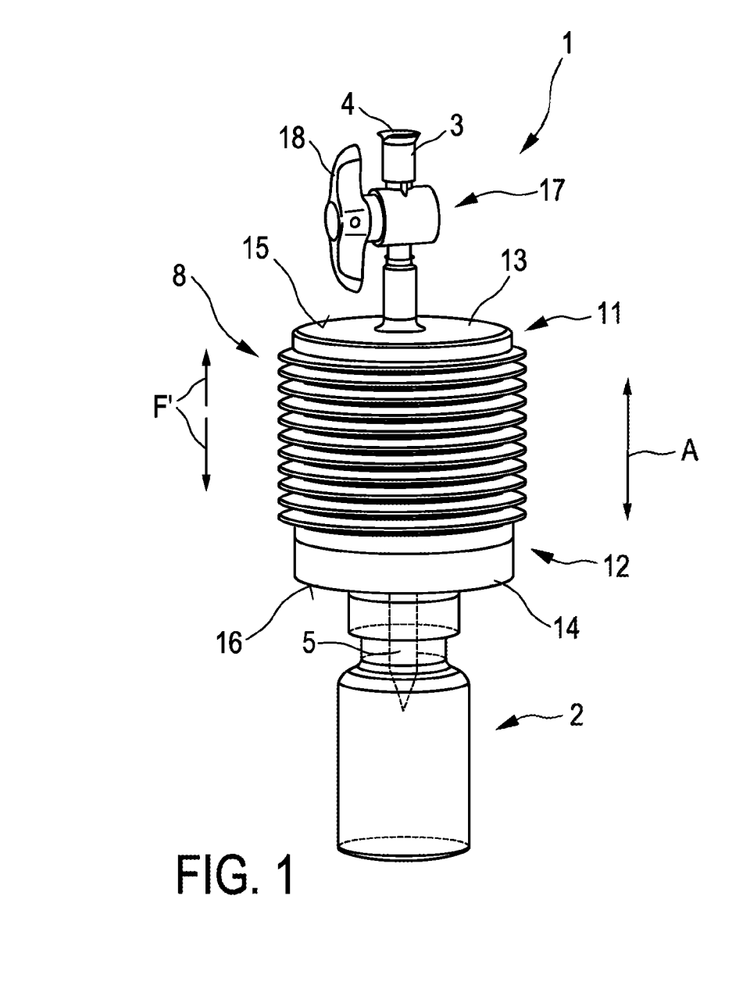
FIG. 1 shows, in a schematic perspective illustration, an embodiment of a medical fluid transfer apparatus according to the invention in a state connected to a medical liquid container.
Figure 2:
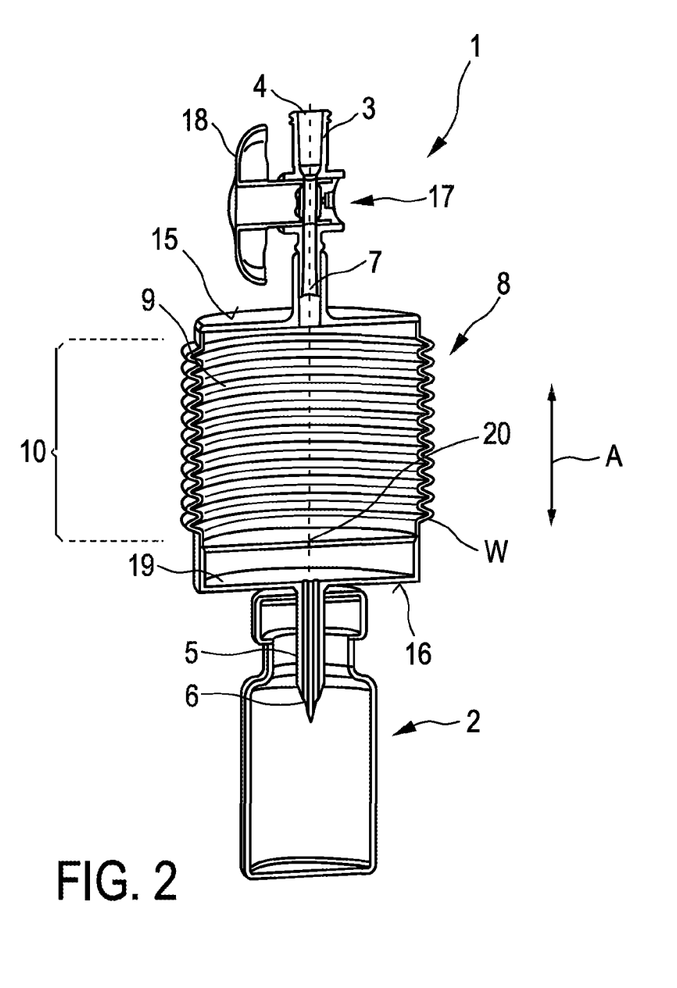
FIG. 2 shows, in a schematic longitudinal sectional illustration, the fluid transfer apparatus plus the liquid container as per FIG. 1.

Extending between the first passage 4 and the second passage 6 is a fluid channel 7, which in FIG. 2 is intended to be illustrated in a schematically highly simplified manner by a dashed line between the first passage 4 and the second passage 6. In a state of the fluid transfer apparatus 1 in which it is connected to the syringe (not illustrated in the drawing) and to the liquid container 2, the liquid medicament F can pass from the syringe into the first passage 4 and, from there, through the second passage 6 via the fluid channel 7 and into the liquid container 2, and vice versa.

In the present case, the liquid container is in the form of a medicament bottle 2, which may also be referred to as ampoule, phial or vial. The medicament bottle 2 may be manufactured from a dimensionally stable material, such as for example a plastic or glass.

The fluid transfer apparatus 1 moreover has a compensation container 8 with a fluid-tight compensation volume 9 of variable volume. The compensation volume 9 is (in a manner that will be described in more detail) connected in a fluid-conducting manner to the liquid container 2 and provided in particular for receiving a gas volume displaced from the liquid container 2 during the transfer of the liquid medicament F.

Here, it can be seen in particular in FIG. 2 that the first passage 4 and the second passage 6 are connected to one another in a fluid-conducting manner via the compensation volume 9, wherein the compensation volume 9 forms a fluid channel section 10 of the fluid channel 7.

If, proceeding from the configuration shown in FIG. 2, liquid medicament F is fed to the liquid container 2 by means of the syringe via the first passage 4, the fluid channel 7 (and the fluid channel section 10) and, from there, through the second passage 6, a displacement of gas volume (not referred to in any more detail) from the liquid container 2 naturally occurs. Said gas volume can be contaminated so as to be hazardous to health through contact with the liquid medicament F. Here, the compensation volume 9 serves for receiving the gas volume in a fluid-tight manner, so that the latter is not released into the surroundings. For this purpose, the compensation volume 9 is (in a manner that will be described in more detail) connected in a fluid-conducting manner to the liquid container 2 and moreover of variable volume. That is to say, when the gas volume flows into the compensation volume 9, the compensation volume is correspondingly enlarged.

The specific configuration, shown in FIGS. 1-6, of the fluid transfer apparatus 1 will be discussed in more detail below. The structural and functional features mentioned additionally in relation to this are not to be regarded as absolutely necessary, however.

In the present case, the compensation container is in the form of a corrugated bellows 8. The corrugated bellows 8 is manufactured from an elastic material W. In the present case, an elastomer is selected as the elastic material W. As a result of the present material selection and the elastic configuration as a corrugated bellows, the compensation container 8 is extensible and compressible in a concertina-like manner in the axial direction A. Owing to this concertina-like movability of the corrugated bellows 8, the compensation volume 9 can be correspondingly varied or enlarged and reduced in size. The corrugated bellows 8 has a circular-cylindrical basic shape, this however not being absolutely necessary.

The first connector section 3 and the second connector section 5 are arranged on face end regions 11, 12 of the corrugated bellows 8 that are situated opposite one another in the axial direction A. For this purpose, in the present case, two housing parts 13, 14 manufactured from a dimensionally stable material (not referred to in any more detail) are provided. At one end, the first housing part 13 is inserted in a fluid-tight manner at a face end side into an axial opening of the corrugated bellows 8. Correspondingly, at the other end, the second housing part 14 is inserted in a fluid-tight manner into an opposite axial opening of the corrugated bellows 8.

The corrugated bellows 8 can be moved manually by way of pumping in the axial direction A. As a result of this movability by way of pumping, the transfer of the liquid medicament F between the first passage 4 and the second passage 6 can (in a manner that will be described in more detail) be brought about and/or assisted.

In order to make possible facilitated manual movability of the corrugated bellows 8 by way of pumping, a first handling surface 15 and a second handling surface 16 are provided in the present case. The first handling surface 15 is arranged on the first housing part 13 and is oriented in the axial direction A. The second handling surface 16 is arranged on the second housing part 14 and is oriented, in the opposite direction to the first handling surface 15, in the axial direction A. For the pumping movement of the corrugated bellows 8, the handling surfaces 15, 16, for example between the fingers of one hand, can be moved toward one another in the axial direction A, wherein the corrugated bellows 8 is pressed together and the compensation volume 9 is correspondingly reduced in size.

Owing to its elastic configuration and/or the present selection of the material W, the corrugated bellows 8 generates a spring force F' (FIG. 1), which is directed oppositely in relation to the above-described pumping movement. The spring force F' is oriented in the axial direction A. Instead of such a configuration, provision may be made for example of a separate spring device and/or a separate spring element which can be connected operatively to the corrugated bellows 8 and/or to the housing parts 13, 14.

Furthermore, a first valve 17 is provided in the present case. The first valve 17 is assigned to the first passage 4 and is arranged in the region of the first connector section 3. The first valve 17 can be transferred between a blocking position (cf. FIG. 4) and a throughflow position (cf. FIG. 3), wherein, in the blocking position, the first passage 4 is separated in a fluid-tight manner from the compensation volume 9 and thus also from the fluid channel section 10. In the throughflow position, the first passage 4 is, by contrast, connected in a fluid-conducting manner to the compensation volume 9 and to the fluid channel section 10.

In the present case, the first valve is in the form of a manually actuatable shut-off valve 17. The shut-off valve 17 has an actuation handle 18. The design in this respect is to be understood purely as an example.

Figure 3:
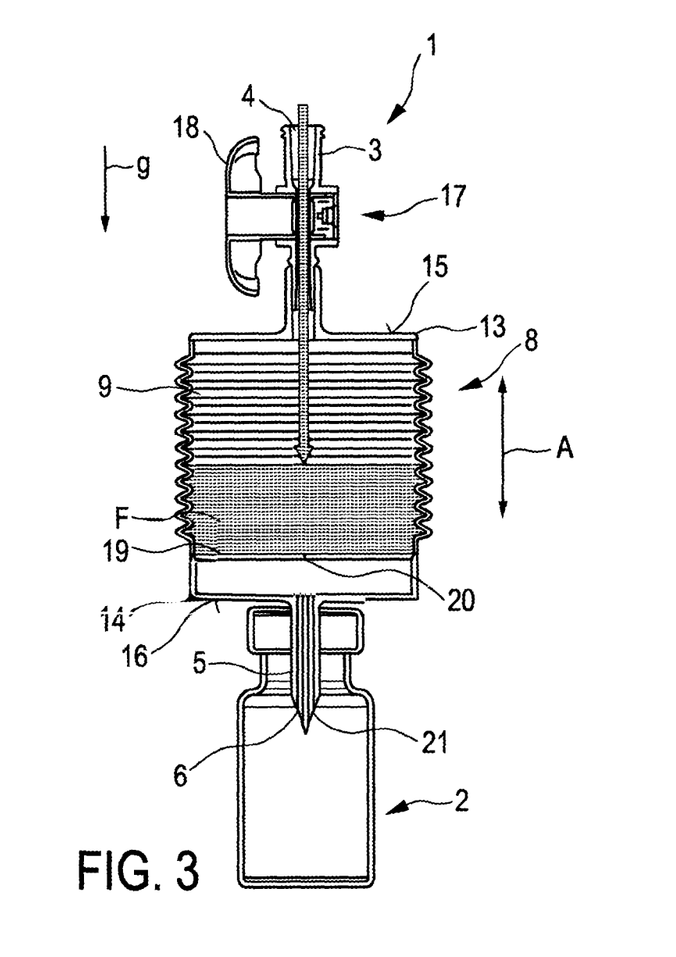
FIGS. 3 and 4 show, in each case in a schematic longitudinal sectional illustration, the fluid transfer apparatus and the liquid container in FIGS. 1 and 2 in different states during the feeding of a health-hazardous liquid medicament into the liquid container.
Figure 4:
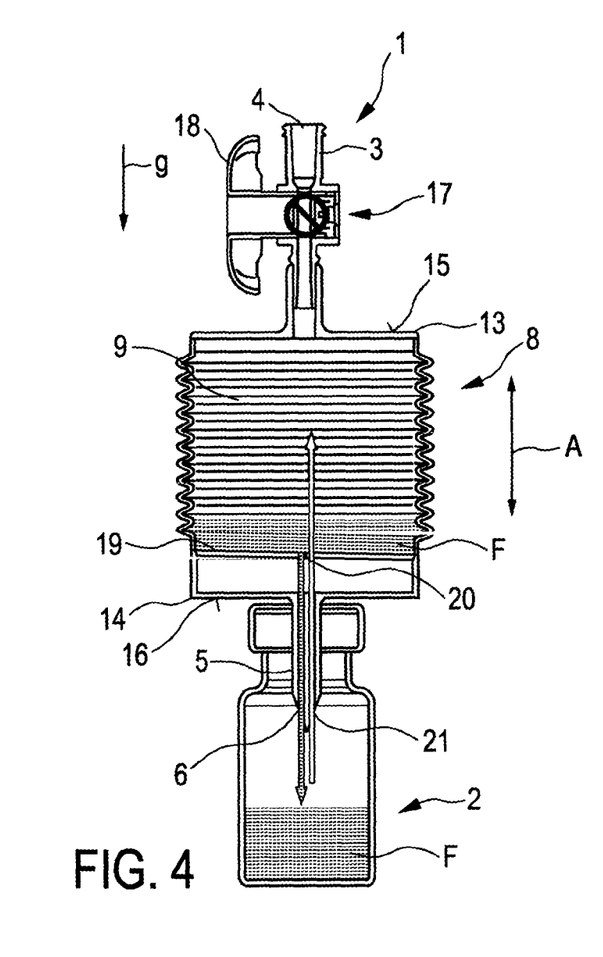

The fluid transfer apparatus 1 furthermore has a second valve 19, which can likewise be transferred between a blocking position (FIG. 3) and a throughflow position (FIG. 4). In the blocking position, the compensation volume 9 is separated in a fluid-tight manner from the second passage 6. By contrast, in the throughflow position, the compensation volume 9 is connected in a fluid-conducting manner to the second passage 6.

In the present case, the second valve is in the form of a pressure valve 19 which, in a manner dependent on a pressure prevailing in the compensation volume 9, can be transferred automatically between the blocking position and the throughflow position. In the present case, the pressure valve 19 is of diaphragm-like design and has a slit-like passage 20 which, in a manner dependent on said pressure in the compensation volume 9, is opened up or closed off as a result of a pressure-induced elastic deformation.

In a delivery state (not illustrated in any more detail in the drawing) of the fluid transfer apparatus 1, both the shut-off valve 17 and the pressure valve 19 assume the respective blocking position. Moreover, the compensation volume 9 is filled with a sterile gas (not referred to in any more detail). As a result of the filling with the sterile gas, which may for example be sterile air, a situation in which the compensation container 8 is undesirably pressed together is avoided.

The functioning of the fluid transfer apparatus 1 during feeding of the liquid medicament F into the liquid container 2 will be described in more detail on the basis of FIGS. 3 and 4.

For this purpose, proceeding from the configuration shown in FIG. 2, firstly a syringe filled with the liquid medicament F is, in the above-described manner, connected in a fluid-tight manner to the first connector section 3. The second connector section in the form of the piercing mandrel 5 is pushed in a fluid-tight manner into the liquid container 2, wherein the second passage 6 extends in a fluid-conducting manner into the interior of the liquid container 2. Here, the shut-off valve 17—in deviation from the configuration shown in FIG. 2—firstly assumes the blocking position and is manually transferred into the throughflow position (FIG. 3) by means of an actuation of the actuation handle 18. Afterwards, the liquid medicament F can be injected through the first passage 4 and into the fluid channel 7 by means of a basically known actuation of the medical syringe, and passes from said fluid channel onward into the fluid channel section 10 or the compensation volume 9. Here, it is advantageous for the axial direction A of the fluid transfer apparatus 1 to be oriented parallel to the Earth's gravity vector g. Such an orientation is not absolutely necessary, however. Through the feeding of the liquid medicament F into the compensation volume 9, a level (shown in FIG. 3 and not referred to in any more detail) of the liquid medicament F is formed in the corrugated bellows 8. The volume of the liquid medicament F that is fed in this manner leads to an expansion of the corrugated bellows 8 in the axial direction A. In the present case, the pressure valve 19 is designed in such a way that, when the liquid medicament F is injected, the slit-like passage 20 firstly remains closed off, so that the pressure valve 19 assumes its blocking position.

Afterwards, the shut-off valve 17 is transferred manually into the blocking position (FIG. 4). In order to transfer the liquid medicament F from the compensation volume 9 into the liquid container 2, the corrugated bellows 8 is compressed by means of the above-described manual actuation of the handling surfaces 15, 16 in the axial direction A. In this way, as a result of a pressure increase in the compensation volume 9, the liquid medicament F is transferred through the slit-like passage 20 and, from there, onward via the second passage 6 into the liquid container 2. In other words, the pressure valve 19 is transferred into its throughflow position as a result of the manual pumping movement of the corrugated bellows 8.

The volume of the liquid medicament F that is fed in this manner to the liquid container 2 naturally leads to a displacement of a gas volume (not referred to in any more detail). Here, the gas volume flows via a fluid-conducting connection into the compensation volume 9 and, owing to the fluid-tight design of the compensation volume 9, is received in a hermetic manner therein without contamination of the surroundings occurring.

The fluid-conducting connection between the compensation volume 9 and the liquid container 2 is realized in the present case by means of a third passage 21, which extends in the form of a lumen through the piercing mandrel 5. Such a design is not absolutely necessary, however.

The manual pumping movement can be repeated until the entire liquid medicament F has been transferred from the compensation volume 9 into the liquid container 2.

Figure 5:
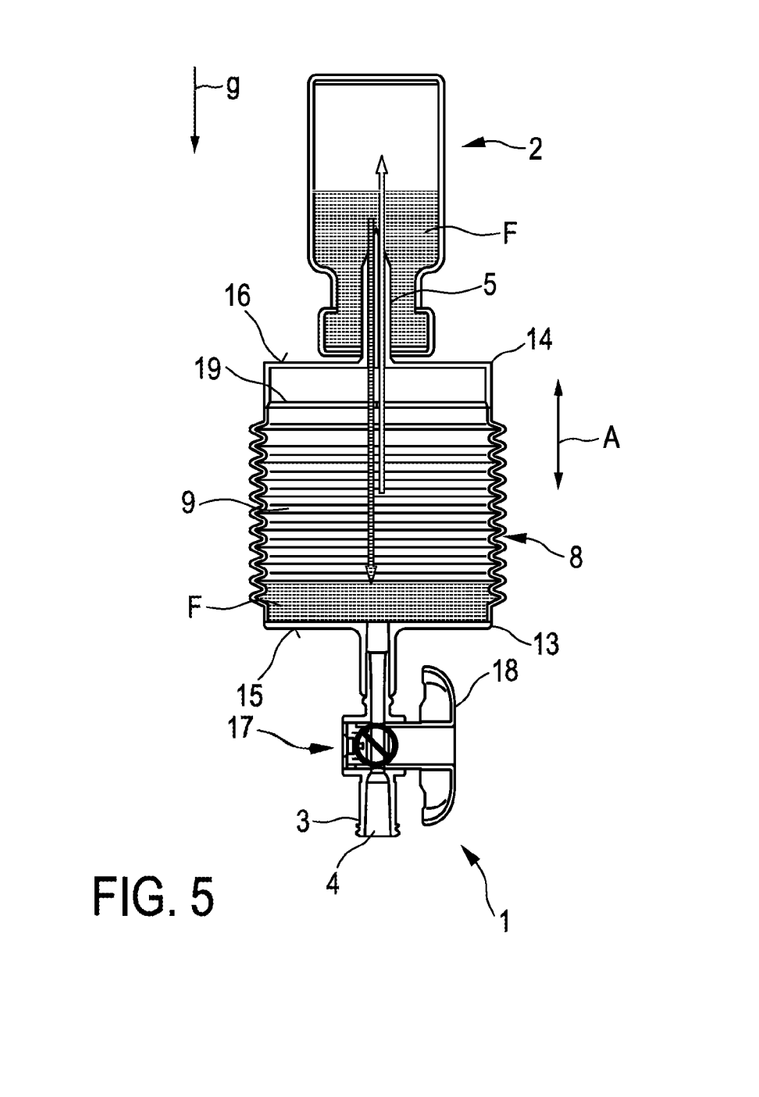
FIGS. 5 and 6 show, in each case in a schematic longitudinal sectional illustration, the fluid transfer apparatus and the liquid container in FIGS. 1-4 in different states during the extraction of the health-hazardous liquid medicament from the liquid container.
Figure 6:
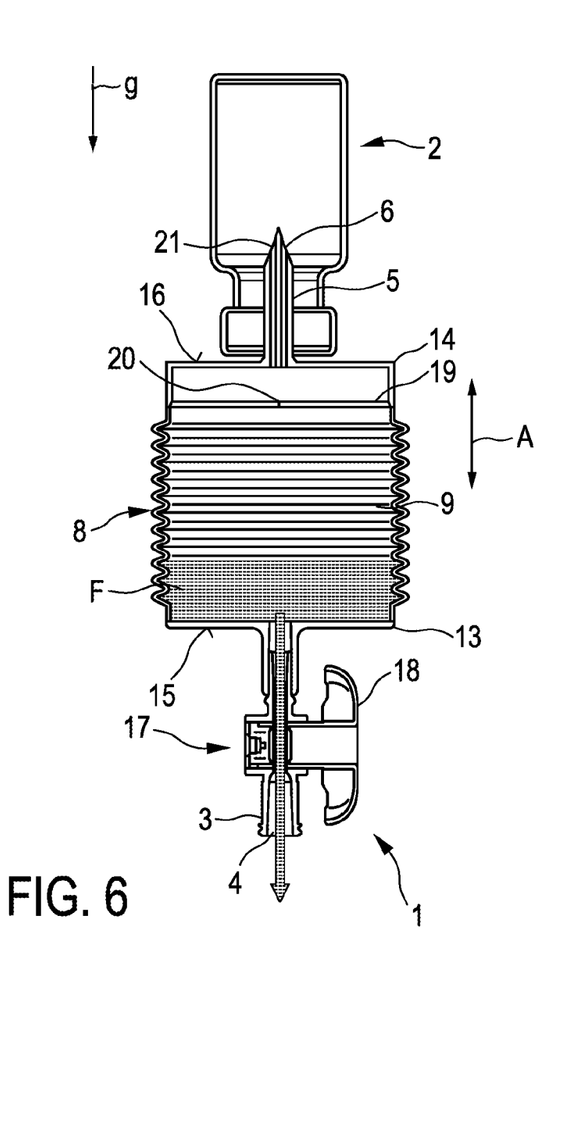

The functioning of the fluid transfer apparatus 1 during extraction of the liquid medicament F from the liquid container 2 can be seen in FIGS. 5 and 6.

Here, proceeding from a configuration in which the liquid container 2 is filled with the liquid medicament F, firstly the second connector section 5 is connected in a fluid-tight manner to the liquid container 2. In the present case, for this purpose, the piercing mandrel 5 is inserted in the above-described manner into the liquid container 2. The shut-off valve 17 in this case assumes its blocking position. Here, the medical syringe may already be connected in a fluid-tight manner to the first connector section 3. Alternatively, this connection may also be realized for the first time at a later point in time.

In the present case, the extraction of the liquid medicament F is realized—just like the feeding illustrated in FIGS. 3 and 4—in two stages. Firstly, the fluid transfer apparatus 1 is oriented, together with the liquid container 2 situated thereon, according to FIG. 5, so that the piercing mandrel 5 points vertically upward counter to Earth's gravity vector g. The corrugated bellows 8 is then pressed together manually in the axial direction A. In this way, the compensation volume 9 is reduced in size and, as a result of the pressure increase brought about in this way, the pressure valve 19 is transferred into the throughflow position. Due to the reduction in size of the compensation volume 9, a gas volume situated therein can pass via the slit-like passage 20 and, from there, onward through the second passage 6 and/or the third passage 21 and into the liquid container 2. In this way, the liquid medicament F situated in said liquid container is displaced and passes via the second passage 6 or the third passage 21 and the slit-like passage 20 into the compensation volume 9. In this way, a level (shown in FIG. 5) of the liquid medicament F is formed in the corrugated bellows 8. This process may be repeated until the liquid container 2 has been substantially emptied.

If it has not already happened, the medical syringe is connected in a fluid-tight manner to the first connector section 3, the shut-off valve 17 is transferred manually into its throughflow position, and the liquid medicament F may be extracted by suction from the compensation volume 9 by means of a corresponding actuation of the medical syringe. Here, the compensation volume 9 is correspondingly reduced in size owing to the volume of the liquid medicament F that is extracted by suction.

Here, it is particularly advantageous that the liquid medicament F, in the configuration shown in FIG. 6, can be readily injected back into the compensation volume 9. In this way, any surplus liquid medicament F or air bubbles present in the medical syringe can be removed from the medical syringe in a simple manner and without having to turn the fluid transfer apparatus 1 over into the orientation shown in FIGS. 3 and 4 beforehand.

Figure 7:
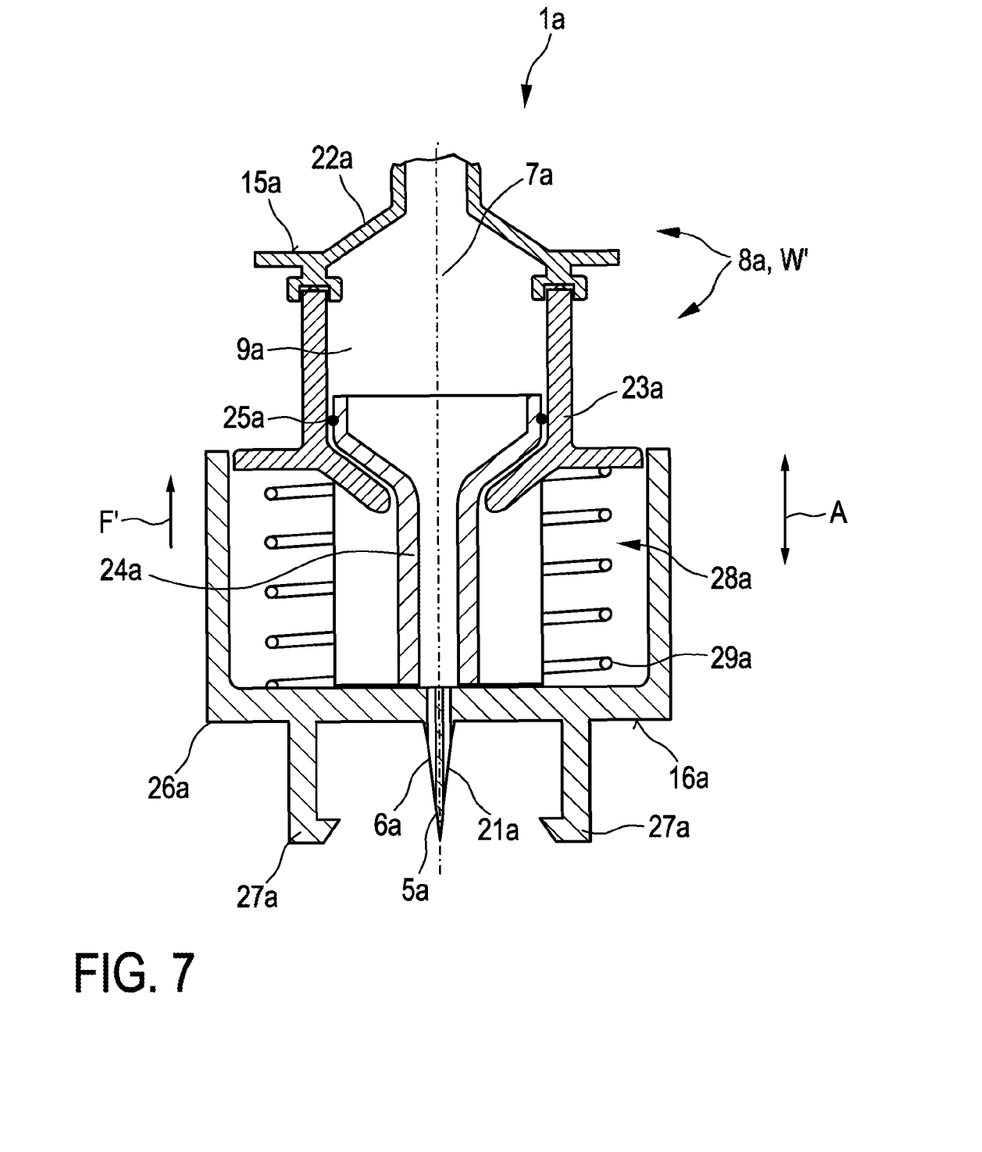
FIG. 7 shows, in a partially cut-away, schematically highly simplified longitudinal sectional illustration, a further embodiment of a medical fluid transfer apparatus according to the invention.

A further embodiment of a fluid transfer apparatus 1a according to the invention can be seen in FIG. 7. The fluid transfer apparatus 1a in FIG. 7 corresponds substantially to the fluid transfer apparatus 1 described above on the basis of FIGS. 1 to 6. Therefore, in order to avoid repetitions, reference is made to the disclosure in relation to FIGS. 1 to 6. Only the essential differences of the embodiment according to FIG. 7 are discussed below. In this case, functionally and/or structurally identical sections and parts of the embodiment according to FIG. 7 are denoted by identical reference-sign numbers with the lower-case letter a added.

The fluid transfer apparatus 1a is primarily distinguished from the fluid transfer apparatus 1 by way of the configuration of the compensation container 8a. In the present case, the compensation container 8a has multiple container parts 22a, 23a and 24a which are manufactured from a dimensionally stable material W'. The container parts 22a, 23a, 24a border the compensation volume 9a. For variation of the volume of the compensation volume 9a, the container parts 22a, 23a are displaceable relative to the container part 24a.

Here, the first container part 22a is, in the form of a cover, joined together in a fluid-tight and fixed manner at a face end side in the axial direction A with the second container part 23a. In the present case, an ultrasonically welded joint is provided as a joining connection, this not however being absolutely necessary. The third container part 24a has, at a face side at one end, a chalice-like widened portion which bears in a fluid-tight manner against an inner wall (not referred to in any more detail) of the second container part 23a and which is slidingly movable relative to said inner wall. For fluid-tight sealing between the second container part 23a and the third container part 24a, a sealing element in the form of an O-ring 25a is provided in the present case.

At the other end, the third container part 24a is joined together in a fluid-tight and fixed manner with a latching device 26a. The latching device 26a is manufactured from a dimensionally stable material (not referred to in any more detail) and is provided for non-detachable latching connection of the fluid transfer apparatus 1 to a liquid container corresponding to the liquid container 2 as per FIGS. 1-6. For this purpose, in the present case, the latching device 26a has multiple latching elements 27a which are provided for form-fitting connection to a neck region of the liquid container 2.

In the present case, the second connector section is again in the form of a piercing mandrel 5a. The piercing mandrel 5a is formed in one piece on the latching device 26a and projects from a cup-like section (not referred to in any more detail) of the latching device 26a at the bottom side in the axial direction A.

The compensation container 8a can again be moved manually by way of pumping. In order to make possible facilitated movability by way of pumping, handling surfaces 15a, 16a are provided. The first handling surface 15a is arranged on the first container part 22a at the top side. The second handling surface 16a is arranged on the latching device 26a at the bottom side.

In order to achieve a simplified return movement of the compensation container 8a in the case of a manual pumping movement, a spring device 28a connected operatively to the compensation container 8a is provided in the present case. The spring device 28a has a spring element in the form of a helical spring 29a which is to be subjected to compressive loading. At one end, the helical spring 29a is supported against the cup-like section of the latching device 26a. At the other end, the helical spring 29a is supported against the second container part 23a at the bottom side.

Further details of the specific design of the container parts 23a and 24a can be seen in FIGS. 8-11.

Figures 8, 9, 10, 11:
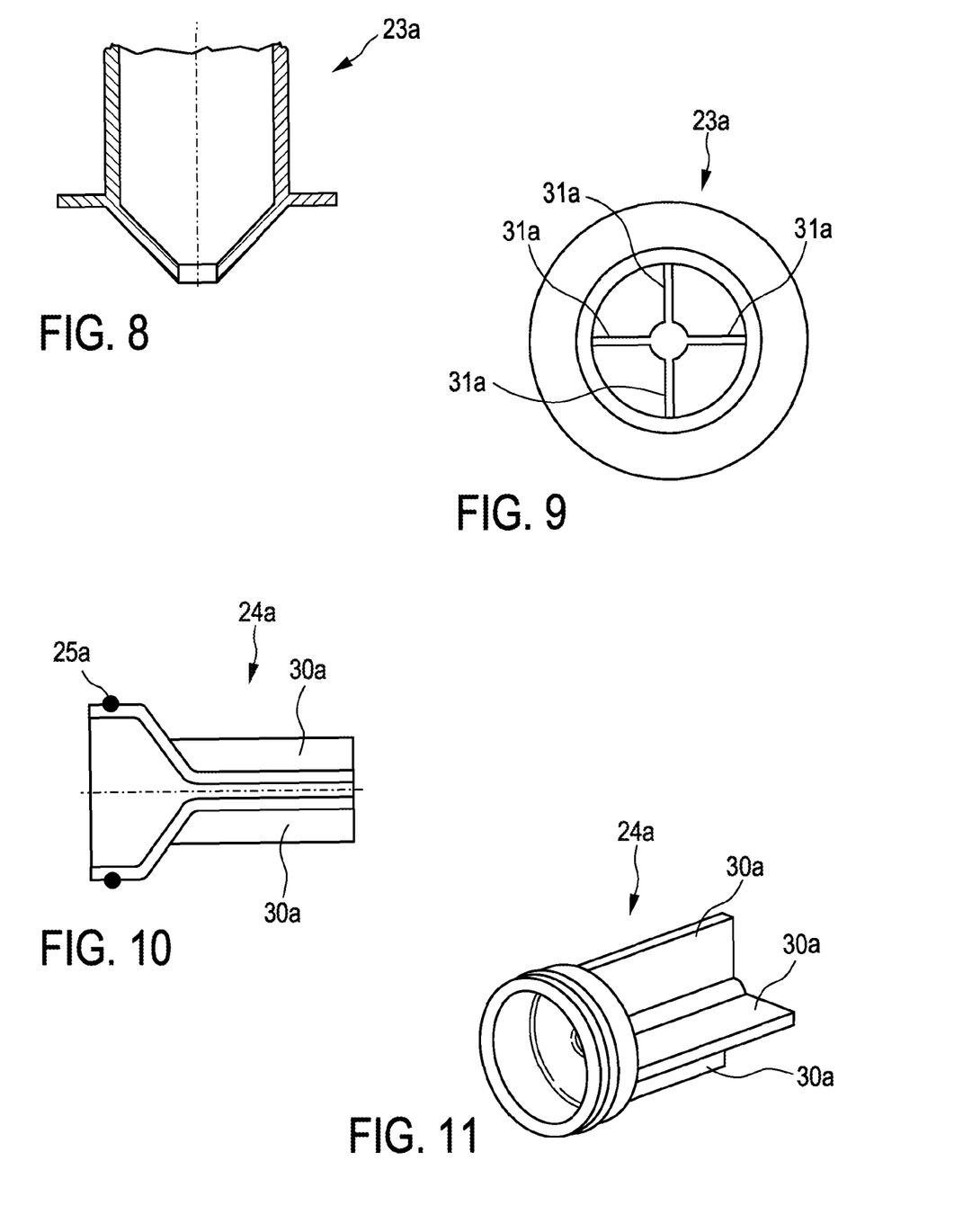
FIG. 8 shows, in a schematic longitudinal sectional illustration, a container part of a compensation container of the fluid transfer apparatus in FIG. 7.
FIG. 9 shows the container part in FIG. 8 in a view directed axially from the top downward.
FIG. 10 shows, in a schematic longitudinal sectional illustration, a further container part of the compensation container of the fluid transfer apparatus in FIG. 7.
FIG. 11 shows the further container part in FIG. 10 in a schematic perspective illustration.

The third container part 24a has in particular multiple wing sections 30a which project in a wing-like manner in a radial direction. In the present case, provision is made of four wing sections 30a, which are in each case arranged offset by 90° in a circumferential direction of the third container part 24a. In FIG. 9, it can be seen that the second container part 23a has a design which is complementary thereto, wherein provision is made of multiple slits 31a for receiving in each case one of the wing sections 30a, which slits are arranged offset in the circumferential direction and extend in a radial direction.

The invention claimed is:

1. A medical fluid transfer apparatus for transferring a liquid medicament that is hazardous in a fluid-tight sealed manner, the medical fluid transfer apparatus comprising:
    a first connector section, which has a first passage and is provided for fluid-tight connection to a medical syringe,
    a second connector section, which has a second passage and a third passage, and which is provided for fluid-tight connection to a medical liquid container,
    a fluid channel, which extends between the first passage and the second passage and allows a fluid-conducting transfer of the liquid medicament between the medical syringe and the medical liquid container when the fluid transfer apparatus is connected to the medical syringe and to the medical liquid container, and
    a compensation container defining a compensation volume that is fluid-tight and variable, which compensation volume is connected in a fluid-conducting manner to the medical liquid container in the connected state of the fluid transfer apparatus by the third passage and is configured for receiving a gas volume displaced from the medical liquid container during the transfer of the liquid medicament,
    the first passage and the second passage being connected to one another in a fluid-conducting manner via the compensation volume, and
    the compensation volume forming a fluid channel section of the fluid channel.

2. The medical fluid transfer apparatus according to claim 1, wherein the first connector section and the second connector section are arranged on face end regions of the compensation container that are situated opposite one another.

3. The medical fluid transfer apparatus according to claim 1, wherein the compensation container is manufactured from an elastic material and/or has an elastic configuration, whereby, for variation of the volume, the compensation volume is elastically expandable and elastically contractable.

4. The medical fluid transfer apparatus according to claim 3, wherein the compensation container is a corrugated bellows.

5. The medical fluid transfer apparatus according to claim 1, wherein the compensation container has at least two container parts that are manufactured from a dimensionally stable material, define the compensation volume between the at least two container parts, and are movable relative to one another, with one of the at least two container parts sliding with another of the at least two container parts, for varying the compensation volume.

6. The medical fluid transfer apparatus according to claim 1, wherein the compensation container is manually movable by pumping for transferring the liquid medicament between the first passage and the second passage.

7. The medical fluid transfer apparatus according to claim 6, further comprising handling surfaces which are connected operatively to the compensation container and which are displaceable relative to one another for manual pumping movement of the compensation container.

8. The medical fluid transfer apparatus according to claim 1, further comprising a spring device which is connected operatively to the compensation container and which imparts a spring force which expands the compensation volume.

9. The medical fluid transfer apparatus according to claim 1, further comprising a first valve which is transferrable between a first blocking position and a first throughflow position and by which the first passage, in the first blocking position, is separated in a fluid-tight manner from the compensation volume and, in the first throughflow position, is connected in a fluid-conducting manner to the compensation volume.

10. The medical fluid transfer apparatus according to claim 9, wherein the first valve is a shut-off valve configured for manual actuation.

11. The medical fluid transfer apparatus according to claim 9, further comprising a second valve which is transferrable between a second blocking position and a second throughflow position and by which the compensation volume, in the second blocking position, is separated in a fluid-tight manner from the second passage and, in the second throughflow position, is connected in a fluid-conducting manner to the second passage.

12. The medical fluid transfer apparatus according to claim 11, wherein the second valve is a pressure valve which, in a manner dependent on a pressure prevailing in the compensation volume, is automatically transferrable between the second blocking position and the second throughflow position.

13. The medical fluid transfer apparatus according to claim 12, wherein the second valve is configured to allow flow in either direction between the first passage and the second passage.

14. The medical fluid transfer apparatus according to claim 12, wherein the second valve is fluidly positioned between the first connector section and the second connector section.

15. The medical fluid transfer apparatus according to claim 12, wherein the second valve comprises a flexible diaphragm having a slit-like passage.

16. The medical fluid transfer apparatus according to claim 11, wherein, in a delivery state of the fluid transfer apparatus, the first valve and the second valve each assume the first blocking position and the second blocking position, respectively, and the compensation volume is filled with a sterile gas.

17. The medical fluid transfer apparatus according to claim 1, further comprising a latching device which is assigned to the second connector section and which allows a non-detachable latching connection to the medicament container.

* * * * *